United States Patent [19]
Fouache née Ducroquet et al.

[11] Patent Number: 5,837,060
[45] Date of Patent: Nov. 17, 1998

[54] PROCESS FOR THE MANUFACTURE OF A STARCH HYDROLYSATE OF LOW POLYMOLECULARITY INDEX, OBTENTION AND USE OF NOVEL STARCH HYDROLYSATE IN PERITONEAL DIALYSIS

[75] Inventors: Catherine Fouache née Ducroquet, Sailly Labourse; Pierrick Duflot, Richebourg, both of France

[73] Assignee: Roquette Freres, Paris, France

[21] Appl. No.: 3,130

[22] Filed: Jan. 6, 1998

Related U.S. Application Data

[63] Continuation of Ser. No. 820,241, Mar. 18, 1997, abandoned, which is a continuation of Ser. No. 388,237, Feb. 14, 1995, abandoned.

[30] Foreign Application Priority Data

Feb. 15, 1994 [FR] France .................................. 94 01707

[51] Int. Cl.[6] .............................. C13K 30/00; C13K 1/06; C13F 3/00; C13D 3/12
[52] U.S. Cl. ................................. 127/36; 127/30; 127/34; 127/40; 127/46.1; 127/55; 536/103
[58] Field of Search ................................. 127/30, 34, 36, 127/40, 46.1, 55; 536/103

[56] References Cited

U.S. PATENT DOCUMENTS

| | | | |
|---|---|---|---|
| 4,846,139 | 7/1989 | Devos et al. | 127/40 |
| 5,424,418 | 6/1995 | Duflot | 536/103 |
| 5,436,329 | 7/1995 | Caboche | 536/103 |

*Primary Examiner*—Mark L. Bell
*Assistant Examiner*—Patricia L. Hailey
*Attorney, Agent, or Firm*—Larson & Taylor

[57] ABSTRACT

The invention relates to a process for the manufacture of a starch hydrolysate of low polymolecularity index which may be used in particular in continuous ambulatory peritoneal dialysis. This process consists essentially in acid and enzymatic hydrolysis of a waxy starch milk and then chromatography on macroporous strong cationic resins of the hydrolysate obtained. The starch hydrolysate is essentially characterized by a polymolecularity index of less than 2.8, a weight-average molecular weight between 5,000 and 22,500 daltons and a number-average molecular weight below 8,000 daltons.

11 Claims, 2 Drawing Sheets

PROCESS FOR THE MANUFACTURE OF A STARCH HYDROLYSATE OF LOW POLYMOLECULARITY INDEX, OBTENTION AND USE OF NOVEL STARCH HYDROLYSATE IN PERITONEAL DIALYSIS

This is a continuation of application Ser. No. 08/820,241 filed Mar. 18, 1997 now abandoned, which is a continuation of Ser. No. 08/388,237 filed Feb. 14, 1995, now abandoned.

The present invention relates to a process for the manufacture of a starch hydrolysate of low polymolecularity index.

More precisely, it relates to a process for the manufacture of a starch hydrolysate of low polymolecularity index which is particularly suitable for the technique of continuous and ambulatory peritoneal dialysis. It also concerns, as a novel product, the starch hydrolysate thus obtained, as well as the use of the said hydrolysate as an osmotic agent in continuous ambulatory peritoneal dialysis.

Standard starch hydrolysates are produced by the acidic or enzymatic hydrolysis of cereal or tuber starch. These hydrolysates are, in fact, a mixture of glucose and glucose polymers, of extremely varied molecular weights.

A first way of classifying them is the measurement of their reducing power, expressed conventionally by the concept of dextrose equivalent or D.E. By definition, a D.E. of 100 is assigned to pure glucose or dextrose, the monomer constituting these polymers. Starch, which is a very large glucose polymer, has a D.E. close to 0. A whole range of starch hydrolysates is found between these two values, the most hydrolysed having a D.E. close to 100 and the least hydrolysed having a D.E. which tends towards 0.

Such a measurement of the D.E. is, however, insufficient for representing precisely the molecular composition of the starch hydrolysate. Thus, for example, maltose, a glucose polymer formed of two molecules of this sugar, which has a degree of polymerization (D.P.) equal to 2 and which has only one reducing end per two molecules of glucose, displays a theoretical D.E. in the region of 50, which is the same as that provided by a mixture in equal parts by weight of starch and glucose.

The acid hydrolysis of starch, which is totally random, or its enzymatic hydrolysis which is slightly more ordered, provide mixtures of glucose and glucose polymers which the D.E. measurement alone does not therefore make it possible to define with precision and which contain very short molecules, of low D.P. as well as very long molecules, of high D.P.

Indeed, measurement of the D.E. gives only an approximate idea of the average degree of polymerization of these polymers and thus of their number-average molecular weight: Mn.

This number-average molecular weight Mn is, in fact, expressed by the equation:

$$M_n = \frac{1}{\Sigma \frac{\text{weight fraction of each molecule}}{\text{molecular weight of this molecule}}}$$

In the example of the mixture in equal parts by weight of starch and glucose, the following is thus obtained:

$$M_n = \frac{1}{\frac{0.5}{180} + \frac{0.5}{\infty}} \text{ i.e. } \frac{180}{0.5} = 360$$

this corresponding to twice the molecular weight of glucose, which is approximately equivalent to the molecular weight of maltose.

As in the case of the D.E., Mn does not make it possible to characterize fully the dispersion of the molecular weights of the polymer mixtures which are the starch hydrolysates, since it too does not enable the difference to be made between maltose and the mixture in equal parts of starch and glucose.

In order to be able to perceive this difference, the weight-average molecular weight: Mw, is then defined, which is expressed by the equation:

$$M_w = \Sigma \text{ weight fraction of each molecule} \times \text{molecular weight of this molecule.}$$

In the example of interest, the following is thus obtained:

Mw: $0.5 \times 180 + 0.5 \times \infty = \infty$, this result being very much removed from the molecular weight of maltose, which is equal to 342, but which in this case gives a good indication of the existence of a large polymer in the mixture.

For simplicity, it is assumed in the foregoing text that starch has an infinite molecular weight. Although it is a very large glucose polymer, its molecular weight is, in reality, finite and is of the order of a few million daltons. Similarly, no account has been taken of the water of reaction required to hydrolyse the polymer fully but which represents only 10% of the weight of the latter and even only 5% of the weight of maltose.

The Mw/Mn ratio is often referred to as the "polymolecularity index" and enables the overall dispersity of the molecular weights of a polymeric mixture to be characterized.

In the ideal case of pure maltose, this ratio is 1; it would tend towards infinity in the case of the mixture in equal parts of starch and glucose.

In practice, the values of Mn and Mw, which allow a better definition of the polymolecular species of which the polymer mixtures are composed, are not calculated but are measured by various techniques. As for the D.E., osmometry, ebulliometry, cryometry, isothermal distillation, the thermoelectric method or the chemical assay of the polymer terminal groups allow access to be gained to Mn. Light scattering allows access to be gained to Mw and occasionally to Mn. Access may also be gained to these two values, Mw and Mn, by gel permeation chromatography, on chromatography columns calibrated with dextrans of known molecular weight (Alsop et al., Process Biochem, 12, 15–22; 1977 or Alsop et al., Chromatography 246, 227–240; 1982). This last method of measurement is very suitable for glucose polymers and is the method used within the context of the present invention.

British Patent Application No. 2,247,242 describes amylose granules which precipitate in aqueous solution, and have a Mn of 4,000 to 7,000 daltons and a particularly low polydispersity index, from 1.4 to 1.7, thus fixing for these granules, a Mw of 5,600 to 11,900 daltons.

European Patent Application No. 207,676 teaches that for use in continuous and ambulatory peritoneal dialysis, starch hydrolysates forming clear and colorless solutions at 10% in water and having a weight-average molecular weight (Mw) from 5,000 to 100,000 daltons and a number-average molecular weight (Mn) below 8,000 daltons are preferred.

Such starch hydrolysates also preferably comprise at least 80% of glucose polymers whose molecular weight is between 5,000 and 50,000 daltons, little or no glucose or glucose polymers of D.P. below or equal to 3 (molecular weight 504) and little or no glucose polymers of molecular weight above 100,000 (D.P. in the region of 600).

In other words, the preferred starch hydrolysates are starch hydrolysates of low polymolecularity index.

It is, indeed, easy to see for this purpose that low-molecular-weight monomers or polymers cross the peritoneal wall rapidly and are hence not of lasting value for the creation of an osmotic pressure gradient, and that very high-molecular-weight polymers, lacking osmotic power, are to be avoided and even forbidden since they are potentially dangerous if they were to precipitate out following their retrogradation.

The processes proposed in this Patent Application for obtaining these starch hydrolysates of low polymolecularity index consist:

either in performing a fractional precipitation of a maltodextrin by means of a water-miscible solvent, or in performing a molecular filtration of this same maltodextrin through various membranes having an appropriate exclusion or cut-off threshold.

In both cases, these processes are aimed at removing both the very-high-molecular-weight polymers and the low-molecular-weight monomers or oligomers.

However, these processes are not satisfactory either from the point of view of their implementation or from the point of view of the yields and quality of the products which they make it possible to obtain.

The reason for this is that they are very intricate to implement since they require the handling of huge volumes of water or, even worse, of expensive and dangerous organic solvents. They are low in yield since they do not make it possible to obtain more than 25% of starch hydrolysate of low polymolecularity index relative to the standard starch hydrolysate used. These processes also do not make it possible to obtain starch hydrolysates whose polymolecularity index is particularly low, although this is desirable for the reasons already outlined above. In European Patent Application No. 207,676, the polymolecularity indices of the products obtained range in effect from 7 to 2.85 in the best of cases.

In the interests of developing a process for the manufacture of a completely water-soluble starch hydrolysate of low polymolecularity index, generally below 7, preferably below 2.8 and even more preferably below 2.5, having an Mn below 8,000 daltons and an Mw between 5,000 and 100,000 daltons, preferably between 8,000 and 50,000 daltons and even more preferably between 12,000 and 20,000 daltons, and which lacks the drawbacks of the prior art, the Applicant Company, which has become engaged in solving this problem, has observed after numerous tests that such a starch hydrolysate could be obtained by carrying out a process consisting in:

acid hydrolysis of a waxy starch milk up to a D.E. between 8 and 15;

optionally, completion of this acid hydrolysis by an enzymatic hydrolysis using bacterial alpha-amylase up to a D.E. between 11 and 18;

chromatography on macroporous strong cationic resins in alkali metal or alkaline-earth metal form of this hydrolysate;

collection of the starch hydrolysate excluded during this chromatography step.

The starch hydrolysate excluded during this chromatography step is preferably collected in a weight yield generally between 10 and 80% of the hydrolysate used in the chromatography step.

The lower the weight yield of the chromatography, the lower is the polydispersity index. Yields of 50% normally correspond to polydispersity indices lower than 2.5.

The process according to the invention makes it possible to obtain completely water-soluble starch hydrolysates of particularly low polymolecularity index. As a novel industrial product, the invention is thus aimed at a waxy starch hydrolysate, characterized in that it has a polymolecularity index below 2.8 and preferably below 2.5, a weight-average molecular weight Mw between 8,000 and 22,500 daltons, preferably between 12,000 and 20,000 daltons, and a number-average molecular weight Mn below 8,000 daltons.

This starch hydrolysate in question preferably contains less than 3% of glucose and of glucose polymers of D.P. below or equal to 3 and less than 0.5% of glucose polymers of D.P. greater than 600.

The Applicant Company has discovered that only starches composed almost exclusively of amylopectin and commonly referred to as waxy starches could be used as starting material in the process of the invention. Cereal starches or tuber starches containing a non-negligible proportion of amylose are not suitable.

The starch used in the process of the invention is preferably a waxy corn starch, but waxy rice starches or waxy tuber starches may also be suitable.

The acid hydrolysis is preferably carried out using hydrochloric acid in a sufficient amount to bring the acidity of the starch milk to a value between 20 and 50 meq/l (milliequivalents per liter). The temperature at which the hydrolysis takes place may be between 105° and 135° C., but it is generally preferred to work under pressure and at a temperature in the region of 117° C. The hydrolysis time is variable and is inversely proportional to the amount of acid used and to the temperature at which this hydrolysis is carried out.

The interdependence of these three parameters is well known to those skilled in the art, who know how to adjust them so that, at the end of this step, a starch hydrolysate whose D.E. is between 8 and 15 is obtained. D.E. values with too large a departure from these values would not make it possible to obtain the starch hydrolysates of low polymolecularity in good yields.

The optional step of enzymatic hydrolysis using bacterial alpha-amylase, is preferably carried out at a temperature between 40° and 100° C. and preferably between 50° and 80° C. Such a step which corresponds especially to the hydrolysis of very high molecular weight products permits, for the same chromatographic yield, to lower the polydispersity index of the products obtained.

The pH of the reaction medium is then adjusted using lime, for example to a value close to the optimum pH of the alpha-amylase employed and which is generally between 5 and 7.

The amount of enzyme employed is preferably between 200 and 2,000 TAU units (Thermostable amylase units) per kilogram of starch used. This non-conventional unit is defined as follows: one TAU unit is the amount of enzyme which, under standard conditions, converts 1 mg of soluble starch per minute into a product having the same absorption power at 620 nm, after reaction with iodine, as a reference colour. These standard conditions are: pH 6.6, temperature 30° C., reaction time 15 to 25 minutes.

The exact procedure for this measurement may be obtained from the company GIST.

It is, however, preferred to use an amount of enzyme between 500 and 1,500 TAU per kilogram of starch, which amount is such that it is not too low, so that the reaction takes place in an acceptable time, and which is such that it is not too high, so as to be able to stop this hydrolysis in time, which hydrolysis, it is reminded, should be ended when a D.E. between 11 and 18, and preferably between 12 and 15 is obtained.

Once again, D.E. values departing too widely from these values would not allow the starch hydrolysates of low polymolecularity which are intended as products of the process according to the invention to be obtained in good yields.

Any process of chemical or physical denaturation of alpha-amylase may be used in order to stop this hydrolysis. However, a physicochemical process is preferably used, and this is conveniently performed by heating the reaction medium to a temperature of 70° to 120° C. for 5 to 60 minutes, after having brought the said medium to a pH below 4.

It is preferable, before performing the ensuing step of chromatography of the reaction medium obtained by acidic and then optionally enzymatic hydrolysis of the waxy starch, to carry out standard filtration and demineralization operations, the aim of which is to remove insoluble or undissolved proteins by means of the physical or chemical treatment of enzymatic denaturation, as well as the inorganic salts or other ionic or non-charged impurities which are contained in the starch used or which have been added in order to carry out the above treatments.

The chromatography step is carried out in a manner which is known per se in relation with other starch hydrolysates. It may be carried out in a batchwise or continuous manner (simulated mobile bed), but should be carried out on adsorbing agents of the macroporous cationic resin type since the Applicant Company has discovered that the cationic resins of gel structure, conventionally used in the fractionation of starch hydrolysates or of the isomerisates thereof, were not suitable for this application. These resins must also be strong cationic resins and they must also be in alkali metal form or optionally in alkaline-earth metal form.

The potassium form $K^+$ is, however, preferred.

This chromatography step may be performed, for example, using the process and apparatus described in American U.S. Pat. No. 4,422,881, of which the Applicant Company is the proprietor. The resins employed as chromatographic adsorbing agent should also preferably have a homogeneous particle size between approximately 100 and 1,500 microns. A preferred particle size is between 200 and 500 microns. One particularly desirable type of resin for carrying out this process is resin C150 in $K^+$ form, marketed by the company PUROLITE.

The choice of the parameters for the chromatographic operation, among which are more particularly noted the relative flow rates for elution, for supply with syrup to be fractionated, that is to say in this case of acidic and then optionally enzymatic waxy starch hydrolysate, the flow rate for extraction of the fraction constituting the starch hydrolysate of low polymolecularity index and the relative flow rate for the fraction essentially combining the low-molecular-weight glucose polymers retained by the resin and, finally, the composition of the regions of desorption, of adsorption and of enrichment when the process and apparatus of American U.S. Pat. No. 4,422,881 are used, is explained and illustrated in the example.

The choice of these parameters is made such that the fraction $X_1$ constituting the starch hydrolysate of low polymolecularity index represents from 10 to 80%, preferably from 30 to 70% and even more preferably from 40 to 60%, of the solids content of the acid-enzyme waxy starch hydrolysate used in this fractionation step.

In order to achieve this result, these parameters are chosen as follows when the chromatographic fractionation is performed according to the teachings of the abovementioned American Patent and when the adsorbing agent used is a macroporous cationic resin crosslinked with about 7.5% of divinyl benzene, of particle size between 400 and 1,200 microns, and when this resin is used in $K^+$ form:

relative elution flow rate of 75 to 750 $1/h/m^3$ of adsorbing agent relative flow rate for supplying with waxy starch hydrolysate, of 10 to 100 $1/h/m^3$ of adsorbing agent relative flow rate for extraction of the fraction $X_1$ constituting the starch hydrolysate of low polymolecularity, of 65 to 650 $1/h/m^3$ of adsorbing agent relative flow rate for extraction of the fraction $X_2$ essentially containing the low-molecular-weight glucose polymers, of 20 to 200 $1/h/m^3$ of adsorbing agent.

The hydrolysis of the waxy starch used in the very specific conditions of the process of the present invention is such that the hydrolysates used in the chromatography step do not noticeably contain glucose polymers whose molecular weight is greater than 200,000 daltons. This greatly simplifies this chromatography step, since it is not necessary to refractionate fraction $X_1$ so as only to retain therefrom the glucose polymers of average size. This fact partly explains the excellent yield of the starch hydrolysate of low polymolecularity which it is possible to obtain by the process of the invention.

Fraction $X_1$ may, in this state or after conventional purifications by decoloration, filtration, demineralization, serve as the basis for the preparation of dialysis solutions because it does not contain insoluble substances, but may also be advantageously modified by chemical or biological processes in order to increase its stability, especially thermic.

Thus, this fraction may be hydrogenated in order to provide polymers whose final glucose reducing end is replaced by a sorbitol non-reducing end.

Such a transformation may be obtained especially by catalytic hydrogenation techniques well known to the persons skilled in the art. These techniques consist, for example, in subjecting a solution of a reducing sugar,in the present case the starch hydrolysate with a low polymolecularity index, in the presence of a Raney nickel catalyst, to a hydrogen pressure of 40 to 70 kg/cm2 and to a temperature of 100° to 150° C. The hydrogenation is continued for some hours until the hydrogenated product shows practically no reducing power.

This fraction $X_1$ may equally be subjected to the action of enzymes extracted especially from bacteria of the type Rhyzobium or Arthrobacter which have the specific activity of isomerizing the maltose reducing terminal bond of polymers obtained by the process of the invention into alpha-alpha trehalose non reducing bonds.

Such an isomerization may be obtained for example thanks to the techniques disclosed in the European Patent Application EP 606,753 whose teachings are incorporated herein by reference. This consists in subjecting a solution of the starch hydrolysate with low polymolecularity index to the action of an enzyme which forms non reducing saccharides at a temperature between 40° and 55° C. and at a pH between 5 and 10. The quasi absence of molecules of low molecular weight (glucose, maltose, maltotriose . . . ) in the products obtained by the process of the present invention, products on which the enzyme is weakly active, permits the obtention of products having only a weak reducing power and which despite everything, are not composed of units of anhydroglucose.

It should be noted here that neither of these two processes, hydrogenation or enzymatic isomerization modifies significantly the Mw, the Mn or the polymolecularity index of the products subjected to these actions. Similarly, the products remain completely soluble in water.

The products of the present invention, even though particularly well adapted as osmotic agents to be used in peritoneal dialysis, whether they be starch hydrolysates of low polymolecularity or their hydrogenated or isomerized equivalents or also usable as very weakly hygroscopic supports for intense sweeteners, for colorants, for flavours, for soluble teas or coffees and may be advantageously used in all cases of traditional use of maltodextrins of low DE, insensitive to retrogradation.

Fraction $X_2$, composed of glucose polymers of low molecular weight, may also be recovered entirely and be hydrolysed fully into glucose, for example, thereby further contributing to the economy of the process of the invention.

This fraction $X_2$ may also be marketed as it is, as a maltodextrin of D.E. in the region of 22, free of relatively heavy glucose polymers.

The aim of the example which follows is to illustrate the invention. It should not constitute a limitation in particular as regards the chromatography step, which is described here only for specific equipment allowing a specific implementation of a continuous process.

Batchwise processes making use of one or more columns may also be used in the process of the invention, as may other continuous systems. The geometry of the devices employed and the efficiency of the piston movements generated within the resins may have an influence on the parameters outlined above, but those skilled in the art will know quickly in which way they should be modified around the average values indicated if the exact installation described here is not available to them.

BRIEF DESCRIPTION OF THE DRAWINGS

FIG. I is a schematic representation of the continuous chromatographic installation of FIG. 2.

EXAMPLE

Acidic liquefaction

A starch milk which is waxy but has a solids content of 320 g/kg at a temperature of 117° C. is liquefied via an acidic route. Hydrochloric acid is used to do this, which is added to the starch milk such that this milk has an acidity of 34 meq/1.

This acidic liquefaction is ended by cooling the hydrolysate as soon as it reaches the D.E. of 11.5.

An Mw of 10.070 and an Mn of 2.020 may then be measured for this hydrolysate. The content of polymers of molecular weight above 100,000 daltons is approximately 0.18%, that of D.P.1, D.P.2, D.P.3 is approximately 7%.

Enzymatic liquefaction

The acid hydrolysate thus obtained is adjusted to a pH of 6.2, its temperature is brought to 65° C. and 0.15°/ . . . by weight of MAXAMYL® bacterial alpha-amylase marketed by the company GIST is added thereto. This enzyme has a specific activity of 6,500 TAU/g. The hydrolysis is allowed to continue until a D.E. of 12.6 is obtained, then the mixture is brought rapidly to 120° C. for 5 minutes in order to denature the enzyme.

It is thus possible to measure for this hydrolysate an Mw of 8,600 and an Mn of 1,650. The content of polymers of molecular weight above 100,000 daltons is no more than about 0.1%. The content of D.P.1+D.P.2+D.P.3 is about 8.5%. This hydrolysate is then filtered, decolorized and demineralized as is the practice for purifying starch hydrolysates.

The entirely clear and colourless syrup obtained, which is reconcentrated to a solids content of 30%, is then ready to undergo the chromatographic fractionation step.

Chromatographic separation

The fractionation of this hydrolysate was carried out in the continuous chromatographic installation whose construction and operation details are described in American U.S. Pat. No. 4,422,881, these details only being repeated here as is necessary for understanding of the process.

Figure 1:
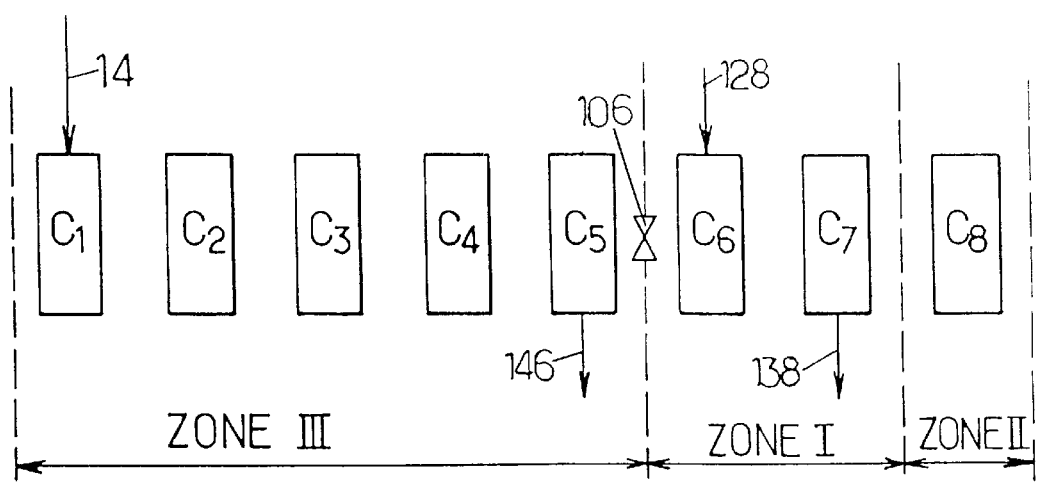
Figure 2:
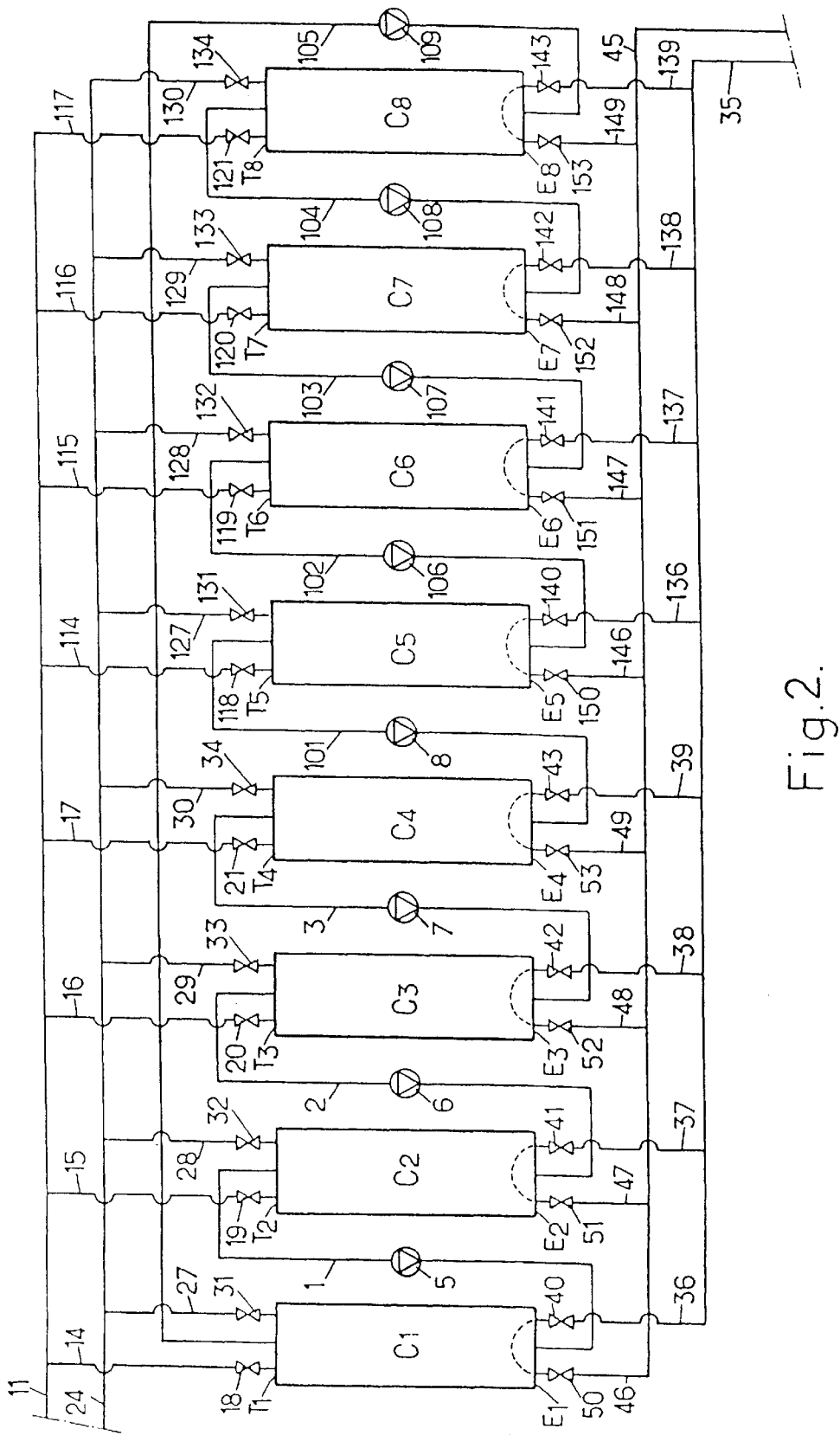
FIG. 2 is the continuous chromatographic installation employed in the present invention.

As shown in FIG. 2 of this American Patent (repeated here as FIG. 1 and for the detailed explanation of which reference will be made to the said American Patent), this installation comprises eight columns or stages $C_1$ to $C_8$ of 200 liters each, filled with C 150 macroporous strong cationic resin marketed by the company PUROLITE, these resins being exchanged into the potassium form, having a particle size between 400 and 1,200 microns and a degree of crosslinking of 7.5%.

By regulation of the electrovalves, a two-stage desorption zone I corresponding to columns 6 and 7, a one-stage adsorption zone II corresponding to column 8 and a five-stage zone III for enrichment and separation of the starch hydrolysate of low polymolecularity index corresponding to columns 1 to 5, are established in this installation, as shown in FIG. 1. This FIG. 1 is a schematic representation of the installation according to FIG. 2, but only the following are featured therein columns $C_1$ to $C_8$, the locking device, in this case electrovalve 106, the tubes for supply of water and of the hydrolysate to be fractionated, which are shown respectively as 128 and 14, and tube 138 for extraction of the glucose and of the low-molecular-weight glucose polymers retained by the resin, on the one hand, (fraction 2), and tube 146 for extraction of the starch hydrolysate of low polymolecularity index (fraction 1).

The locking device 106 maintains, in the adopted configuration, total leakproofing between zone III, on the one hand, which is a zone for enrichment with high-molecular-weight polymers at the end of which the starch hydrolysate of low polymolecularity index is recovered by the tube 146, and, on the other hand, the zone I for desorption of the glucose and the low-molecular-weight glucose polymers, at the head of which zone the desorption water is introduced.

This locking device 106 determines the direction of passage of the liquid phase through the resin.

A timer set to 1,500 seconds provides the following flow rates:

Water, via tube 128, 366 liters/hour

The hydrolysate at a solids content of 30%, via tube 14, 50 liters/hour

Starch hydrolysate of low polymolecularity index, via tube 146, 326 liters/hour

Glucose and low-molecular-weight glucose polymers, via tube 138, 90 liters/hour.

After 1,500 seconds, all the inlets and outlets, as well as the locking device 106, are shifted to the right.

These flow rates are established such that after 1,500 seconds the amount of the hydrolysate is compatible with the volume of adsorbing resin and its adsorption capacity.

Similarly, the amount of water admitted during this time is that which makes it possible to desorb virtually all of the glucose and the low-molecular-weight polymers which have been adsorbed by the resin.

The relative share of the yield with respect to glucose polymers of low polymolecularity index and to low-molecular-weight products is provided by the ratio of the outlet flow rates of pipes 146 and 138. Under the conditions adopted within the context of this example, the weight yield of glucose polymers of low polymolecularity index is substantially equal to 50% of the solids content introduced into the chromatographic system.

An increase in this yield, which would be obtained by increasing the flow rate of outlet 146, would be reflected in the production of a product whose polymolecularity index would be raised and whose Mw and Mn would be decreased.

A reduction in this yield would, obviously, achieve the opposite result.

In order to carry out this chromatography, the temperature within the columns is maintained at 75° C.

Fraction $X_1$, which, under these conditions, is composed in reality of one part of pure water originating from the elution of the resin column of the previous cycle, is split into two sub-fractions. The first sub-fraction, representing the first 700 seconds of the cycle of 1,500 seconds, also equivalent to the first 63.5 liters of each cycle, is composed of practically pure water which is not recovered.

The second part of this fraction, which flows out of the installation via outlet 146 between the 701st second and the end of each 1,500-second cycle is recovered in order to undergo an additional purification. This is the fraction which, at a solids content of about 4.5%, constitutes the starch hydrolysate of low polymolecularity index.

This fraction, which cannot be used as it is, must, for its application in continuous and ambulatory peritoneal dialysis, undergo the purification treatments which follow but which have no influence on the Mw, the Mn or the polymolecularity index of the product obtained after the chromatography step.

It is of course possible, to precede these purification treatments by catalytic hydrogenation treatments or by enzymatic isomerization as have already been described earlier.

Purification

The second part of fraction $X_1$ derived from the chromatography step, optionally hydrogenated or isomerized, is concentrated under vacuum to a solids content of 35%. It is then demineralized on an array of ion-exchange resins consisting of a strong cationic resin which is exchanged into hydrogen form, a weak anionic resin which is exchanged into hydroxyl form and a mixed bed of strong cationic and anionic resins which are also in $H^+$ and $OH^-$ form. The demineralization is carried out under conditions, especially of flow rate, such that a resistivity of greater than $10^6$ ohms.cm is obtained for the syrups.

After the demineralization, the syrup is treated with 1% of ACTICARBON 3S charcoal marketed by the company CECA, in order to remove pyrogenic substances.

This syrup is then filtered on bacteriological filters of mesh size 0.22 micron in order to sterilize it, and it is then sprayed under rigorous aseptic conditions, to give a perfectly white, odourless and tasteless powder.

This starch hydrolysate of low polymolecularity index gives the following analysis:

The content of D.P.+D.P.2+D.P.3 is 1%, the content of glucose polymers of molecular weight above 100,000 daltons is less than 0.25%.

Mw 14,600
Mn 6,300
Mw/Mn=2.3

The extremely low polymolecularity index of the product obtained by the process according to the invention will be noted.

As a guide, the analysis of fraction $X_2$ which combines glucose and glucose polymers of low molecular weight gave the following analysis:

Mw 4,400
Mn 870

The starch hydrolysate of low polymolecularity index thus purified and dehydrated is then readily dissolved along with other electrolytes, to give osmotic agents of extremely high performance in continuous and ambulatory peritoneal dialysis.

We claim:

1. Process for the manufacture of a starch hydrolysate of polymolecularity index below 7, comprising:
    (a) subjecting a waxy starch milk that is a milk containing a starch composed almost exclusively of amylopectin to acid hydrolysis to produce an acid hydrolysate having a DE of between 8 and 15;
    (b) submitting the hydrolysate thus obtained to a chromatographic separation on macroporous strong cationic resins in alkali metal or alkaline-earth metal form; and
    (c) collecting the starch hydrolysate excluded during this chromatographic step.

2. Manufacturing process according to claim 1, wherein the acid hydrolysate is subjected to an enzymatic hydrolysis using bacterial alpha-amylase, said acid hydrolysate a DE having between 11 and 18 before being submitted to the chromatographic separation.

3. Manufacturing process according to claim 1, wherein the starch hydrolysate excluded during the chromatographic step is collected in a yield between 10 and 80% of the hydrolysate used in the chromatographic step.

4. Manufacturing process according to claim 1, wherein the chromatographic separation is carried out on resins in potassium form.

5. Manufacturing process according to claim 1, wherein the excluded starch hydrolysate is subjected to a thermal stabilization step consisting in a catalytic hydrogenation or in an enzymatic isomerization transforming the reducing ends into trehalose.

6. A waxy starch hydrolysate, completely water-soluble, having a polymolecularity index below 2.8, a weight-average molecular weight (Mw) between 8,000 and 22,500 daltons and a number-average molecular weight (Mn) below 8,000 daltons.

7. A waxy starch hydrolysate, according to claim 6 which is, in addition, hydrogenated or isomerized.

8. A waxy starch hydrolysate according to claim 6, having a polymolecularity index below 2.5.

9. A waxy starch hydrolysate according to claim 6, having a weight-average molecular weight (Mw) between 12,000 and 20,000 daltons.

10. A waxy starch hydrolysate according to claim 6, having less than 3% of glucose and glucose polymers of DP less than or equal to 3, and less than 0.5% of glucose polymers of DP greater than 600.

11. Osmotic agent for use in continuous and ambulatory peritoneal dialysis, consisting of a waxy starch hydrolysate according to claim 6.

* * * * *